United States Patent [19]
Goswami et al.

[11] Patent Number: 6,160,139
[45] Date of Patent: Dec. 12, 2000

[54] PROCESS FOR THE OXIDATION OF PSEUDODIOSGENIN DIACETATE TO DIOSONE FOR THE PRODUCTION OF 16-DEHYDROPREGNENOLONE ACETATE

[75] Inventors: Amrit Goswami; Rumi Kataky; Ramesh Chandra Rastogi; Anil C. Ghosh, all of Assam, India

[73] Assignee: Council of Scientific & Industrial Research, New Delhi, India

[21] Appl. No.: 09/048,279

[22] Filed: Mar. 26, 1998

[51] Int. Cl.$^7$ ........................................................ C07J 7/00
[52] U.S. Cl. .............................................................. 552/606
[58] Field of Search ............................................ 552/606

[56] References Cited

PUBLICATIONS

Abstract –Kavtardge, L.K., Gruz, S S R, I.A.N., Khim, S. *Chemical Abstracts*, 1985, vol. 103, 123771e.

Abstract (US Patent 3,136,758) –Chemorda, J.M., Ruyle, W.V. and Mendell, L., *Chemical Abstracts*, 1964, vol. 61, 7081a.

Abstract (US Patent 2,409,293) –Marker, R.H., *Chemical Abstracts*, 1947, vol. 41, 1396f.

Specification (British Pat. 749,697) –Hewett, C.L., Improvements in the Production of Pseudo–Sapogenin Compunds, *Chemical Abstracts*, 1957, vol. 51, 28097.

Article –Hazra, B.G., Chordia, M.D., Bahule, B.B., Pore, V.S. and Basu, S., Manganese–mediated Novel Dibromination of Olefins with Tetradecyltrimethyl–ammonium Permanganate and Trimethylbromosilane, *National Chemical Laboratory (NCL) Communication*, No. 5407, p. 16, 1994.

Abstract –Micovic, I.V., Ivanovic, M.D. and Platak, D.M., Simplified Preparation of 16–Dehydropregnenolene Acetate, *Synthesis*, Jul. 1990, p. 591.

*Primary Examiner*—Barbara Badio
*Attorney, Agent, or Firm*—Michael D. Bednarek; Shawpittman

[57] ABSTRACT

The invention relates to a process for the production of 16-dehydropregnenolone acetate of the formula

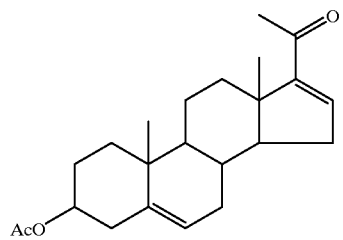

comprising the oxidation of pseudodiosgenin diacetate in the presence of a phase transfer catalyst at a temperature between 0–15° C. to produce diosone followed by the hydrolysis and degradation of diosone to produce 16-dehydropregnenolone acetate.

10 Claims, 1 Drawing Sheet

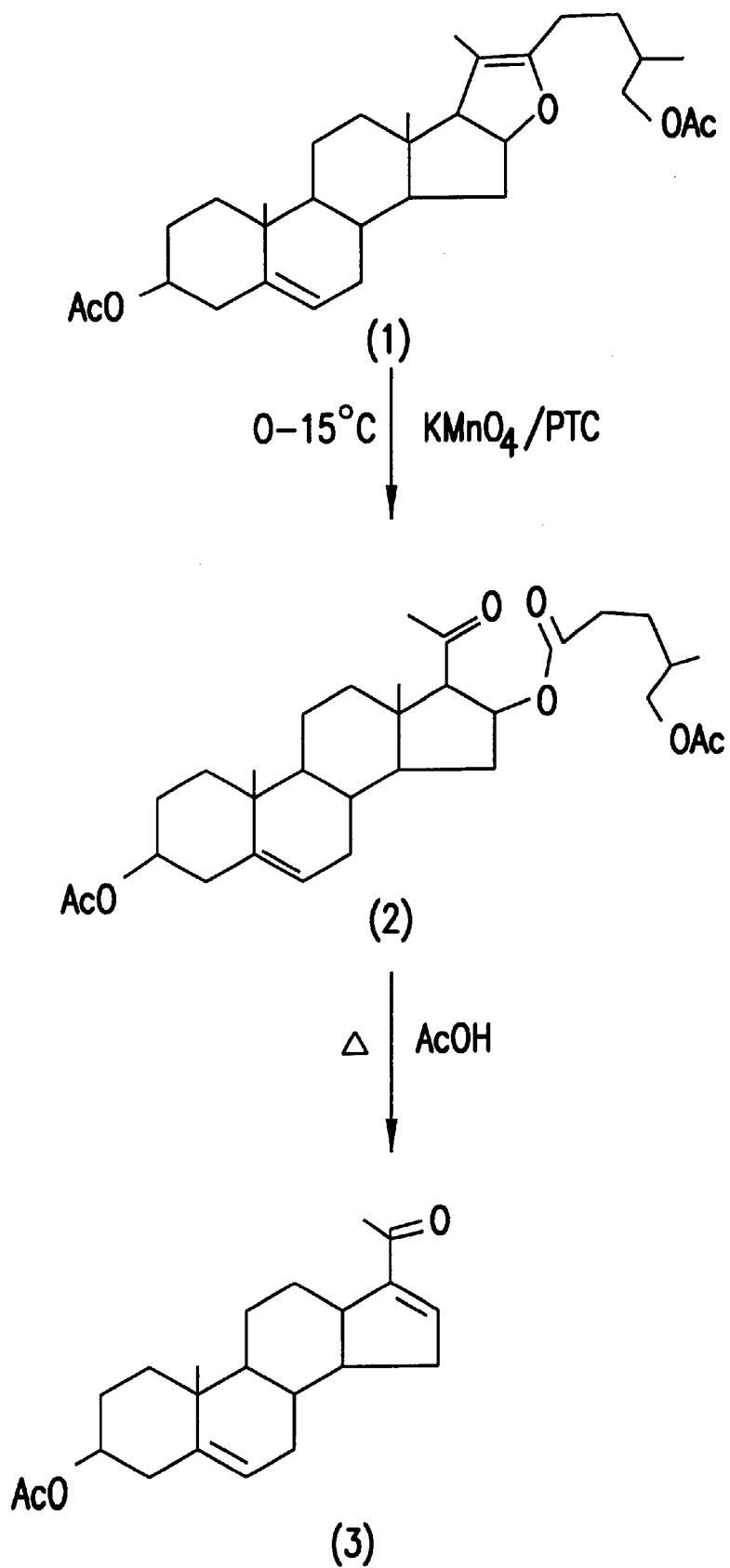

PROCESS FOR THE OXIDATION OF PSEUDODIOSGENIN DIACETATE TO DIOSONE FOR THE PRODUCTION OF 16-DEHYDROPREGNENOLONE ACETATE

This invention relates to an improved process for the oxidation of pseudodiosgenin diacetate of the formula (1) to produce diosone of the formula (2) which is finally converted to 16-dehydroprognenolone acetate of the formula (3). The invention particularly, relates to an improved oxidation process using an environmentally friendly catalyst to avoid conventionally used toxic chromium catalyst. The process of the present invention does not involve the use of any high boiling liquid nor any costly or environmentally toxic catalysts. The recovery of the solvent is also possible which makes the process simple and economic. The process of the present invention has been developed using a very non toxic low cost and low boiling less polar organic solvents under normal atmospheric pressure.

BACKGROUND OF THE INVENTION

The hitherto known processes for the preparation of diosone of the formula (2). Where Ac represents acetyl group have been described below.
i) Marker R. H, U.S. Pat., No. 2,409,293 1947. Chem. Abstr. 41, 1396f In this method pseudodiosgenin diacetate of the formula (1) where Ac represents an acetyl group is oxidized with chromium trioxide in acetic acid at 28° C. to get diosone of the formula (2) where Ac represents an acetyl group.
ii) Colin L. Hewatt. British Pat. 749, 697, May 30, 1956 Chem Abstr. 51, 1957, 28907.

In this method steroidal sapogenin or esters were converted first to pseudosapogenin which is then converted to pseudodiosgenin and finally the pseudodiosgenin is again oxidized with chromium trioxide to get pregnalien-3-ol-20 one acetate.
iii) John, M. Chemorda; William, V. Ruyle and Leon, Mendell. U.S. Pat. No. 3,136,758, (Cl 260–239.55) 1964. Chem Abstr. 61, 7081Q.

In this method 5,6-dichlorodiosgenin was oxidized with chromium trioxide in acetic acid and water to get 5,6-dichloro 16-dehydropregnenolone acetate.
iv) Ngo, Ngoc Khuyen, Nguyen, Van Dan. Tap Chi Hoa Hec 1976, 14 (1) 37–39 (Vietnam) Chem Abstr. 88, 191216z.

In this method 16 Dehydropregnenolone acetate (3) was prepared by boiling a solution of diosgenin in acetic anhydride and pyridine hydrochloride, cooling, adding aqueous sodium acetate followed by oxidation with potassium dichromate and boiling with aqueous sodium bisulphite extracting with petroleum ether to get the product.
v) Kavtardge L. K. Izv Akad Nauk Gruz S S R, Ser Khim 1984, 10 (3) 229–31 (Russ). Chem Abstr. 103, 123771e.

In this method too tigogenin is converted by conventional method to pseudodiosgenin and finally pseudodiosgenin is oxidized with chromium trioxide in acetic acid to give 3-hydroxy-5-pregnen-16-en-20-one.
vi) Micovic, I. V. Ivanovic, M. D and Platak, D. M. Synthesis, 1990, 591.

In this method diosgenin is converted to pseudodiosgenin diacetate by refluxing with acetic anhydride in presence of ammonium chloride and pyridine and pseudodiosgenin diacetate (PDA) is again oxidized by conventional method using chromium trioxide and acetic acid at 0–150° C. to diosone which is finally hydrolysed by refluxing it in acetic acid to get 69% 16-dehydroprenenolone acetate.

In all these methods the major drawback is that the oxidizing agent contains chromium which is highly poisonous, costly and not echo friendly.

OBJECT OF THE INVENTION

The major objective of the present invention is to provide an improved process for the preparation of diosone of the formula (2) from pseudodiosgenin diacetate of the formula (1) avoiding the drawbacks summarized above in the hitherto known processes. Another object of the present invention is to provide an improved process for the production of diosone of the formula (2) eliminating the use of expensive and environmentally toxic conventional chromium catalysts and to make the production of diosone to commercially produce 16-dehydropregnenolone acetate (16-DPA) in a feasable and economical way.

Yet another object of the present invention is to provide an improved process for the preparation of diosone of the formula (2) to produce 16-DAP of the formula (3) by avoiding the use of high boiling solvents in the process so as to avoid the recovery of such solvents which is energy intensive and consequently making the process for the commercial production of 16-DPA economical.

Still yet another object of the present invention is to provide an improved process for the production of diosone of the formula (2) from pseudodiosgenin diacetate of the formula (1) having a yield of 81% to produce 16-DAP of the formula (3) in 65–70% yield. The simplicity of the reaction using very cheap and environmentally friendly catalyst with promising yield of diosone of the formula (2) and hence 16-DAP of the formula (3) makes the process commercially viable and important.

DESCRIPTION OF THE DRAWINGS

FIG. 1 is a schematic drawing illustrating the improved process for the production of 16-DPA of the present invention.

DETAILED DESCRIPTION OF THE INVENTION

Accordingly, the present invention provide an improved process for the production of 16 DPA of the formula (3) shown in the drawing accompaying this specification which comprises (a) Oxidation of the pseudodiosgenin diacetate of the formula (1)using a phase transfer catalyst selected from tetramethyl ammonium iodide and tetra-methyl ammonium iodide at a temperature ranging from 0–15° C. to produce diosone of the formule (2)

(b) Hydrolysis and degradation of diosone of the formula (2) so obtained to produce 16 DPA of the formula (3).

In a preferred embodiment of the present invention the oxidation of pseudodiosgenin diacetate of the formula (1) where Ac represent an acetyl group, can be effected using potassium permanganate and the like. The solvent used for such reaction is selected from dichloromethane, benzene, toluene, acetonitrile, tetrahydrofuran, acetone, ethanol, methanol and the like.

We have also found that when the oxidation of pseudodiosgenin diacetate of the formula (1) is done with potassium permanganate in presence of sodium sulphate at room temperature the yield of diosone is found to be around 72%. Further the oxidation reaction becomes environmentally more friendly due to the use of potassium permanganate. We have also observed that when equimolar amount of potassium permanganate and the substrate are taken the reaction proceeds in half way. An excess amount of potassium permanganate is required and the excess amount is found to be almost one mole. The temperature employed during the oxidation step ranges from 0–15° C. The oxidation procedure described above is a novel one and we have made this oxidation procedure for the production of the diosone from pseudodiosgenin diacetate.

The details of the process disclosed in this invention have been described in the following specific examples which are provided to illustrate the invention only and therefore these should not be construed to limit the scope of the present invention.

EXAMPLES

Examples 1

(a) Oxidation of pseudodiosgenin diacetate of the formula (1) to diosone of the formula (2) in benzene.

50 gms (0.1 mole) of pseudodiosgenin diacetate of the formula (1) was dissolved in 75 ml of benzene and taken it with about 60–70 ml water in a one litre 3 necked flask fitted with a mechanical stirrer and dropping funnel on an ice bath. To this solution added 0.5 gms (1%) of tetra ethylammonium iodide. Dissolved 31.7 gms (0.2 mole) of potassium permanganate in about 75 ml water and added dropwise to the pseudodiosgenin diacetate solution in 30 minutes. The pH of the reaction mixture was maintained at 3 by adding sodium acetate/acetic acid buffer. The mixture was vigorously stirred maintaining the bath temperature at 0–15° C. Occasionally TLC was observed to monitor the progress of the reaction. After 2.5 hours the conversion was found to be complete. It was then filtered and the product was isolated in benzene from the filtrate. Dried the solvent and distilled it out under vacuum to get a gummy material:Yield: 40.06 gms (80.12%).

(b) Hydrolysis of diosone of the formula (2) to 16-DPA of the formula (3). 40.06 gms of diosone (2) was refluxed with 150 ml of glacial acetic acid for 3 hours. The progress of the reaction was monitored on TLC. When TLC indicated complete conversion of diosone to 16-DPA it was stopped and acetic acid was distilled out under vacuum to get a crude gummy mass of 16-DPA of the formula (3). It was isolated by extracting the crude in petroleum ether and crystallized in methanol. Yield of 16-DPA: 21.24 gms (79% with respect to diosone and 60% with respect to pseudodiosgenin diacetate); Melting point: 171° C.; Specific rotation (–)42.4.

Example 2

(a) Oxidation of pseudodiosgenin diacetate (1) to diosone (2) in dichloromethane. 34 gms (0.06 mole) of pseudodiosgenin diacetate (1) was dissolved in about 100 ml of dichloromethane and placed it in a 3 necked round bottomed flask fitted with a mechanical stirrer on an ice bath. To it added 0.34 gms (1%) of tetra ethyl ammonium iodide as phase transfer catalyst. Added about 75 ml water to the pseudodiosgenin diacetate solution. Dissolved 20 gms potassium permanganate (0.1.2 mole) in about 100 ml water and added to the reaction mixture dropwise in 30 minutes. Maintain the pH of the reaction mixture at around 3 by adding sodium acetate/acetic acid buffer. Progress of the reaction was monitored on TLC. Full conversion of pseudodiosgenin diacetate was found to be about within 1.5 hour. After completion of the reaction it was neutralized with sodium biocarbonate and filtered. The filtrate was extracted in dichloromethane and washed with fresh water and then dried over anhydrous sodium sulphate. Solvent was removed under vacuum to get a gummy material. Yield: 27 gms (75%).

(b) Hydrolysis of diosone (2) to 16-dehydropregnenolone acetate (3)

27 gms of diosone (2) was refluxed with 150 ml of glacial acetic acid for 3–4 hours. When TLC indicated full conversion, acetic acid was distilled out under reduced pressure. 16-DAP (3) was isolated from the crude mass by extracting it with petroleum ether. Yield=17 gms (94% with respect to diosone and 71% with respect to pseudodiosgenin diacetate. Melting point 170° C.: Specific rotation (–) 42.4.

Example 3

(a) Oxidation of pseudodiosgenin diacetate (1) to diosone (2) in acetone.

Same procedure was followed as described in example 1(a).

Solvent used: Acetone; Pseudodiosgenin diacetate: 1 gm; Potassium permanganate: 0.63 gm; Tetra ethyl ammonium iodide: 0.01 gm Reaction time: 2 hours. pH 3; Yield of diosone 0.11 gm (10.38%).

(b) Hydrolysis of diosone to 16-DAP (3).

Same procedure was followed as described in example 1 (b) Yield of 16-DPA (3): 0.035 gm (50% w.r.t. diosone and 4.9% w.r.t. pseudodiosgenindiacetate).

Example 4

(a) Oxidation of pseudodiosgenin diacetate (1) to diosone (2) in tetrahydrofuran.

Same procedure was followed as described in example 1 (a). Pseudodiosgenin diacetate: 1 gm; Potassium permanganate: 0.63 gm: Tetra ethyl ammonium iodide: 0.01 gm; Solvent: Tetrahydrofuran: 10 ml Reaction time: 2 hours; pH: 3. Yield of diosone: 0.48 gm (45/28%).

(b) Hydrolysis of diosone (2) to 16-DAP (3)

Same procedure was followed by dissolving 0.48 gm of diosone in 20 ml glacial acetic acid. Yield of 16-DPA (3): 0.22 gm (68.7% w. r. t. diosone and 31% w. r. t. pseudodiosgenin diacetate).

Example 5

(a) Oxidation of pseudodiosgenin diacetate (1) to diosone (2) in acetonitrile.

Same procedure was followed as described in example 1 (a) Pseudodiosgenin diacetate (1): 1 gm; Potassium permanganate: 0.63 gm Acetonitrile: 10 ml; Tetra ethyl ammonium iodide: 0.01 gm. Duration of the reaction: 2 hours: pH: 3. Yield of diosone (2): 0.8 gm (75%).

(b) Hydrolysis of diosone (2) to 16-DPA (3) =p Same procedure was followed as described in example 1 (b) by refluxing 0.8 gm diosone in 20 ml glacial acetic acid. Yield of 16-DPA (3): 0.46 gm (87% w. r. t. diosone and 55% w. r. t. pseudodiosgenin diacetate).

Example 6

(a) Oxidation of pseudodiosgenin diacetate (1) to diosone (2) in methanol.

Same procedure was followed as described in example 1 (a) Pseudodiosgenin diacetate: 1 gm; Potassium permanganate: 0.63 gm; Tetra ethyl ammonium iodide: 0.01 gm; Methanol: 10 ml. Duration of reaction: 2 hours: pH: 3 Yield of diosone (2): 0.5 gm (45%).

(b) Hydrolysis of diosone (2) to 16-DAP (3).

Same procedure was followed as described in example 1 (b) Diosone: 0.5 gm Glacial acetic acid 10 ml: Refluxing time: 3 hours. 16-DPA was crystallized from methanol. Yield of 16-DPA: 0.25 gm (75% w. r. t. diosone, 35.2% w. r. t. pseudodiosgenin diacetate).

Example 7

(a) Oxidation of pseudodiosgenin diacetate (1) to diosone (2) in ethanol.

Same procedure was followed as described in example 1 (a) Pseudodiosgenin diacetate: 1 gm; Potassium permanganate: 0.63 gm Tetra ethyl ammonium iodide: 0.01 gm; Ethanol: 10 ml; Reaction time: 2 hours pH: 3. Yield of diosone (2): 0.46 gm (42.5%).

(b) Hydrolysis of diosone (2) to 16-DPA (3)

Same procedure was followed as described in example 1 (b) by refluxing 0.46 gm of diosone (2) in 20 ml of glacial acetic acid. Yield of 16-DPA (3): 0.21 gm (70% w. r. t. diosone 29.5% w.r.t. pseudodiosgenin diacetate).

Example 8

(a) Oxidation of pseudodiosgenin diacetate (1) to diosone (2) in presence of tetramethyl ammonium iodide.

Same procedure was followed as described in example 1 (a) Pseudodiosgenin diacetate: 1 gm: Potassium permanganate: 0.63 gm, Tetraethyl ammonium iodide: 0.01 gm; Solvent: Dichloromethane: 10 ml pH: 3. Duration of the reaction: 2.5 hours: Reaction temp. 0–1 5° C. Yield of diosone (2): 0.78 gm (73%).

(b) Hydrolysis of diosone (2) to 16-DAP (3)

Same procedure was followed as described in example 1 (b) by refluxing 0.78 gm diosone (2) in 20 ml glacial acetic acid. 16-DPA obtained was purified by recrystallization in ethanol. Yield: 0.38 gm (73% w. r. t. diosone, 53.5% w. r. t. pseudodiosgenin diacetate).

ADVANTAGES OF THE PRESENT INVENTION

The main advantages of this invention are (1) It is a one pot reaction; For example pseudodiosgenin diacetate, phase transfer catalyst and the buffer solution were taken together and to it potassium permianganate solution was added slowly at 0–15° C. and the mixture was stirred for 1–2.5 hours.

(2) The oxidising agent used is echo friendly and is very cheap.

(3) Practically no side product formation was observed.

(4) It is an easy method for production of 16-DAP of the formula (3) with a better yield.

We claim:

1. An improved process for the production of 16-dehydropregnenolone acetate which comprises (a) oxidation of pseudodiosgenin diacetate of the formula

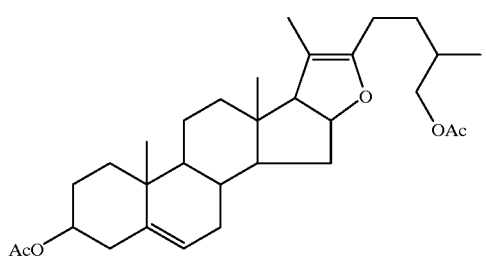

using a phase transfer catalyst selected from the group consisting of tetramethyl ammonium iodide and tetraethyl ammonium iodide at a temperature range between 0–15° C. to produce diosone of the formula

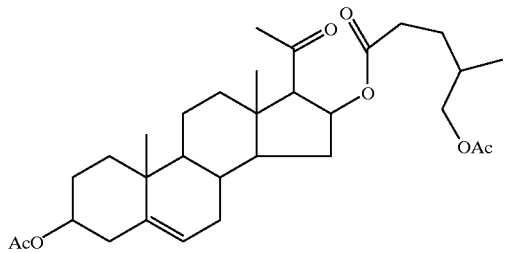

(b) hydrolysis and degradation of diosone of the formula

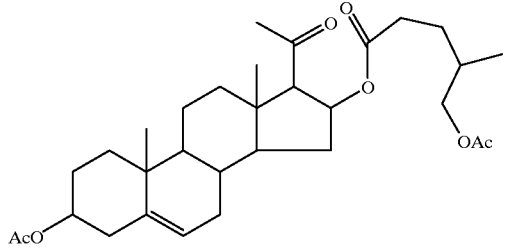

so obtained to produce 16-dehydropregnenolone acetate.

2. An improved process as claimed in claim 1 wherein the oxidation is effected by potassium permanganate as an oxidizing agent.

3. An improved process as claimed in claim 1, wherein the solvent used for oxidation is selected from dichloromethane benzene, tetrahydrofuran, acetonitrile, ethanol, methanol and acetone.

4. An improved process as claimed in claim 1, wherein the reaction is performed in both single and two phase system using water and both water miscible and immiscible organic solvents.

5. An improved process as claimed in claim 4, wherein diosone of the formula

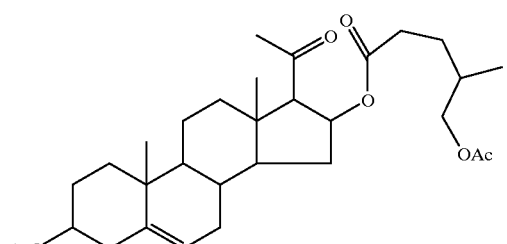

obtained is extracted in dichloromethane or with any other water immiscible and less polar organic solvents.

6. An improved process as claimed in claim 1, wherein diosone of the formula

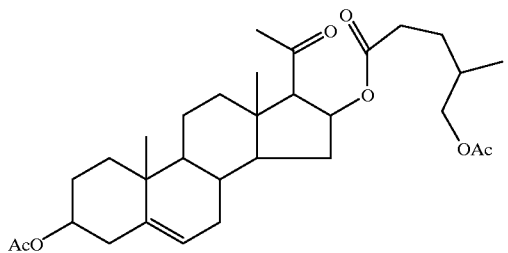

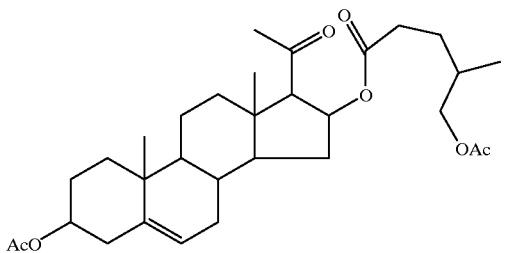

obtained is hydrolysed with a mild organic acid selected from the group consisting of formic acid, acetic and propionic acid.

7. An improved process as claimed in claim 1, wherein the hydrolysis of diosone of the formula

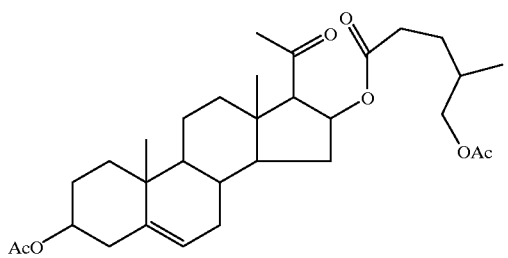

is effected at a temperature ranging from 110–150° C.

8. An improved process as claimed obtained by hydrolysis of diosone of the formula is extracted in petroleum ether.

9. An improved process as claimed in claim 1, wherein 16-dehydropregnenolone acetate is crystallized in methanol or ethanol.

10. An improved process as claimed in claim 1, wherein the molar ratio of pseudodiosgenin diacetate of the formula

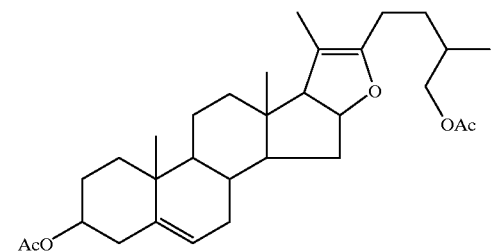

and the oxidizing agent should be 1:2.

* * * * *